(12) United States Patent
Hirao et al.

(10) Patent No.: US 7,615,628 B2
(45) Date of Patent: Nov. 10, 2009

(54) IMIDAZOPYRIDINE DERIVATIVES

(75) Inventors: Ichiro Hirao, Yokohama (JP); Shigeyuki Yokoyama, Yokohama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 11/795,554

(22) PCT Filed: Jan. 17, 2006

(86) PCT No.: PCT/JP2006/300502

§ 371 (c)(1),
(2), (4) Date: Dec. 7, 2007

(87) PCT Pub. No.: WO2006/077816

PCT Pub. Date: Jul. 27, 2006

(65) Prior Publication Data

US 2008/0125381 A1    May 29, 2008

(30) Foreign Application Priority Data

Jan. 20, 2005    (JP) ............................. 2005-012685

(51) Int. Cl.
*C07H 19/00* (2006.01)
*C07H 19/22* (2006.01)

(52) U.S. Cl. .................. 536/27.1; 536/27.11; 536/27.13

(58) Field of Classification Search ........................ None
See application file for complete search history.

(56) References Cited

U.S. PATENT DOCUMENTS

| 4,996,308 A | 2/1991 | Edwards et al. |
| 2004/0063658 A1 | 4/2004 | Roberts et al. |

FOREIGN PATENT DOCUMENTS

| JP | 1-283285 A | 11/1989 |
| JP | 6-56877 A | 3/1994 |
| JP | 2005-232079 A | 9/2005 |
| WO | WO-03/093290 A2 | 11/2003 |

OTHER PUBLICATIONS

Hocek et al., Collect Czech CHem Commun., 2001, vol. 66, pp. 483-499.*

Cristalli et al., Nucleosides and NUcleotides, 1991, vol. 10, No. 1-3, pp. 253-257.*
Hocek M. et al., Collect. Czech. Chem. Commun., 2001, vol. 66, pp. 483-499.
Cristalli G. et al., Nucleosides & Nucleotides, 1991, vol. 10, No. 1-3, pp. 253-257.
Cristalli G. et al., J. Med. Chem., 1991, vol. 34, pp. 2226 to 2230.
Cristalli G. et al., J. Med. Chem., 1987, vol. 30, pp. 1686-1688.
Bergman AM. et al., Nucleosides & Nucleotides, 1999, vol. 18, No. 4 & 5, pp. 897-898.

* cited by examiner

*Primary Examiner*—Traviss C McIntosh, III
(74) *Attorney, Agent, or Firm*—Birch, Stewart, Kolasch & Birch, LLP

(57) ABSTRACT

The present invention relates to a novel imidazo[4,5-b]pyridine derivative compound represented by Formula (I) and a pharmaceutically acceptable salt thereof. The present invention also relates to a method for preparing the above compound. The present invention further relates to a pharmaceutical composition comprising the above compound. The above compound has growth inhibitory activity on cancer cells, and this effect is dissociated from growth inhibitory activity on normal cells. This indicates that the compound is useful as a novel anticancer agent.

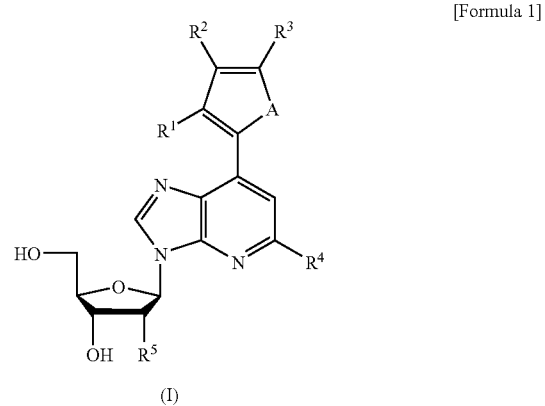

[Formula 1]

(I)

9 Claims, No Drawings

IMIDAZOPYRIDINE DERIVATIVES

TECHNICAL FIELD

The present application is a National Stage entry of PCT/JP2006/300502 filed on Jan. 17, 2006, to which priority is claimed under 35 U.S.C. § 120, and priority is also claimed to Japanese patent application 2005/01265 filed Jan. 20, 2005 under 35 U.S.C. § 119.

This application claims priority to a Japanese patent application filed on Jan. 20, 2005 under Japanese Patent Application No. 2005-012685, the entire contents of which are incorporated herein by reference.

The present invention relates to novel imidazo[4,5-b]pyridine derivative compounds and their pharmaceutically acceptable salts. The present invention also relates to a method for preparing the above compounds. The present invention further relates to pharmaceutical compositions comprising the above compounds, which can be used as anticancer agents.

BACKGROUND ART

Although various drugs have been used as anticancer agents, many problems remain in terms of their applicability and side effects, etc. For this reason, there is a demand for the development of new drugs. Hocek et al. (Collect. Czech. Chem. Commun., Vol. 66, pp. 483-499 (2001)) have synthesized 6-arylpurine nucleoside derivatives, and have demonstrated that these derivatives have cell growth inhibitory activity on various cancer cell lines. Also, the inventors of the present invention have synthesized purine nucleosides having various heterocyclic rings as a substituent at the 6-position of the purine ring, and have analyzed these compounds for their anticancer effect (JP 2005-232079 A (Japanese Patent Application No. 2004-43377 filed on Feb. 19, 2004, which was not yet published at the priority date of the present application)).

To be useful as anticancer agents, it is highly desired that drugs have a property such that they act on cancer cells to inhibit their growth and/or function, while they do not have such activity on normal cells or such activity is weak on normal cells.

All documents cited herein are incorporated herein by reference in their entirety.

Patent Document 1: JP 2005-232079 A (Japanese Patent Application No. 2004-43377, filed on Feb. 19, 2004)

Non-patent Document 1: M. Hocek, et al., Collect. Czech. Chem. Commun., Vol. 66, pp. 483-499 (2001)

DISCLOSURE OF THE INVENTION

Problems to be Solved by the Invention

The present invention provides novel imidazo[4,5-b]pyridine derivatives, i.e., a 3-(2-deoxy-β-D-ribofuranosyl)-3H-imidazo[4,5-b]pyridine derivative and a 5-amino-3-(2-deoxy-β-D-ribofuranosyl)-3H-imidazo[4,5-b]pyridine derivative, each of which has a heterocyclic ring as a substituent at the 7-position. The imidazo[4,5-b]pyridine derivatives of the present invention are compounds represented by Formula (I) shown below:

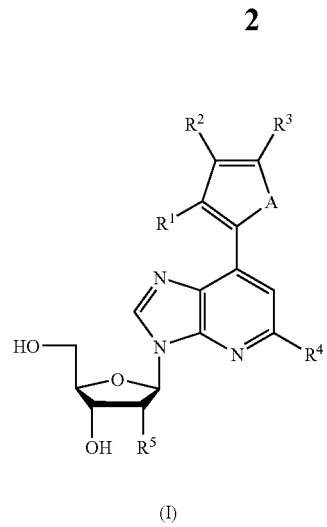

[Formula 1]

(I)

[wherein A represents an oxygen atom or a sulfur atom;
R$^1$, R$^2$ and R$^3$ each independently represent a hydrogen atom or a C$_1$-C$_4$ alkyl group;
R$^4$ represents a hydrogen atom or an amino group; and
R$^5$ represents a hydrogen atom or a hydroxyl group]

or a pharmaceutically acceptable salt thereof.

The present invention also provides a method for preparing a compound of Formula (I) according to the present invention or a pharmaceutically acceptable salt thereof. The method comprises treating a compound represented by Formula

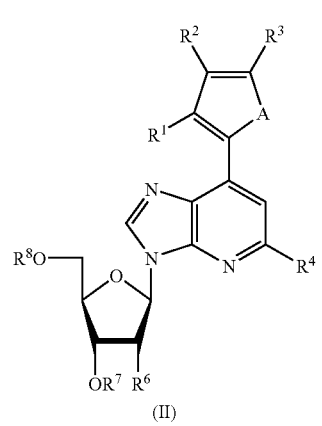

[Formula 2]

(II)

[wherein A represents an oxygen atom or a sulfur atom;
R$^1$, R$^2$ and R$^3$ each independently represent a hydrogen atom or a C$_1$-C$_4$ alkyl group;
R$^4$ represents a hydrogen atom or an amino group;
R$^6$ represents a hydrogen atom or a R$^9$O group; and
R$^7$, R$^8$ and R$^9$, which may be the same or different, each represent a protecting group for a hydroxyl group selected from the group consisting of an acetyl group, an isobutyryl group, a benzoyl group, a p-toluoyl group, a benzyl group, a trityl group, a dimethoxytrityl group and a t-butyldimethylsilyl group]

with ammonia, methanolic ammonia, potassium hydroxide, sodium hydroxide, sodium methoxide, sodium ethoxide, hydrochloric acid, trifluoroacetic acid, tetrabutylammonium fluoride, boron tribromide, or hydrogen/palladium catalyst.

The present invention further provides an intermediate for preparing a compound of Formula (I) according to the present invention. The intermediate is a compound represented by Formula (II):

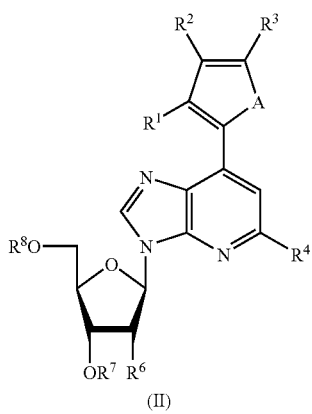

[Formula 3]

(II)

[wherein A represents an oxygen atom or a sulfur atom;

$R^1$, $R^2$ and $R^3$ each independently represent a hydrogen atom or a $C_1$-$C_4$ alkyl group;

$R^4$ represents a hydrogen atom or an amino group;

$R^6$ represents a hydrogen atom or a $R^9O$ group; and $R^7$, $R^8$ and $R^9$, which may be the same or different, each represent a protecting group for a hydroxyl group selected from the group consisting of an acetyl group, an isobutyryl group, a benzoyl group, a p-toluoyl group, a benzyl group, a trityl group, a dimethoxytrityl group and a t-butyldimethylsilyl group].

Moreover, the present invention provides a pharmaceutical composition comprising a compound of Formula (I) according to the present invention. The present invention provides a compound of Formula (I) which can be used as an anticancer agent.

Means for Solving the Problems

As a result of extensive and intensive efforts made to solve the problems stated above, the inventors of the present invention have succeeded in synthesizing a novel imidazo[4,5-b]pyridine derivative compound represented by Formula (I), and have found that the compound has cell growth inhibitory activity on cancer cells. Moreover, the inventors have found that this cancer cell growth inhibitory effect is dissociated from cell growth inhibitory activity on normal cells. This means that a novel imidazo[4,5-b]pyridine derivative compound represented by Formula (I) has properties desirable as an anticancer agent in that the compound has a cell growth inhibitory effect on cancer cells and has a weaker cell growth inhibitory effect on normal cells. Based on this finding, the inventors have concluded that the compound is useful as an anticancer agent, and have completed the present invention.

The present invention provides novel imidazo[4,5-b]pyridine derivatives, i.e., a 3-(2-deoxy-β-D-ribofuranosyl)-3H-imidazo[4,5-b]pyridine derivative and a 5-amino-3-(2-deoxy-β-D-ribofuranosyl)-3H-imidazo[4,5-b]pyridine derivative, each of which has a heterocyclic ring as a substituent at the 7-position. The imidazo[4,5-b]pyridine derivatives of the present invention are each a compound represented by Formula (I) shown below:

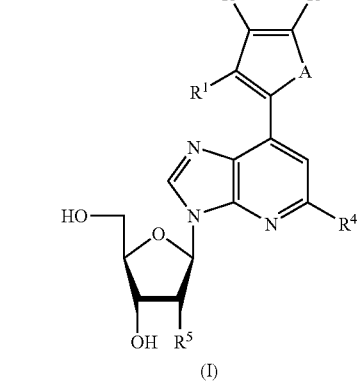

[Formula 4]

(I)

[wherein A represents an oxygen atom or a sulfur atom;

$R^1$, $R^2$ and $R^3$ each independently represent a hydrogen atom or a $C_1$-$C_4$ alkyl group;

$R^4$ represents a hydrogen atom or an amino group; and $R^5$ represents a hydrogen atom or a hydroxyl group] or a pharmaceutically acceptable salt thereof. In the above imidazo[4,5-b]pyridine derivatives of the present invention represented by Formula (I), A is preferably a sulfur atom. Likewise, in the above imidazo[4,5-b]pyridine derivatives of the present invention represented by Formula (I), any one of, desirably any two of, and more desirably all three of $R^1$, $R^2$ and $R^3$ are each preferably a hydrogen atom. The imidazo[4,5-b]pyridine derivatives of the present invention are more preferably compounds of Formula (I) shown above wherein A is a sulfur atom, and any one of, desirably any two of, and more desirably all three of $R^1$, $R^2$ and $R^3$ are each a hydrogen atom.

Among compounds of Formula (I), a compound wherein $R^4$ is a hydrogen atom, i.e., a 3-(2-deoxy-β-D-ribofuranosyl)-3H-imidazo[4,5-b]pyridine derivative having a heterocyclic ring as a substituent at the 7-position of the imidazo[4,5-b]pyridine ring is also represented herein by Formula (Ia). Likewise, among compounds of Formula (I), a compound wherein $R^4$ at the 5-position of the imidazo[4,5-b]pyridine ring is an amino group, i.e., a 5-amino-3-(2-deoxy-β-D-ribofuranosyl)-3H-imidazo[4,5-b]pyridine derivative having a heterocyclic ring as a substituent at the 7-position is also represented herein by Formula (Ib).

In one embodiment of the present invention, the compound of Formula (I) according to the present invention is a compound selected from the group consisting of:

7-(2-thienyl)-3-(2-deoxy-β-D-ribofuranosyl)-3H-imidazo[4,5-b]pyridine;

5-amino-7-(2-thienyl)-3-(2-deoxy-β-D-ribofuranosyl)-3H-imidazo[4,5-b]pyridine; and pharmaceutically acceptable salts thereof.

The present invention also provides a method for synthesizing a compound of Formula (I) according to the present invention or a pharmaceutically acceptable salt thereof.

In one embodiment of the present invention, a 3-(2-deoxy-β-D-ribofuranosyl)-3H-imidazo[4,5-b]pyridine derivative of Formula (Ia) according to the present invention, which has a heterocyclic ring as a substituent at the 7-position, may be synthesized through the synthetic pathway shown in the following reaction scheme (Scheme I):

[Formula 5]

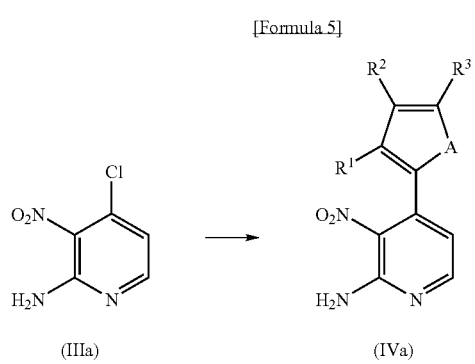

(IIIa) → (IVa)

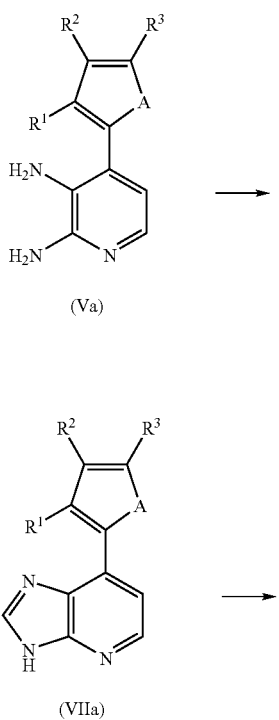

(Va) → (VIIa) → (IIa) →

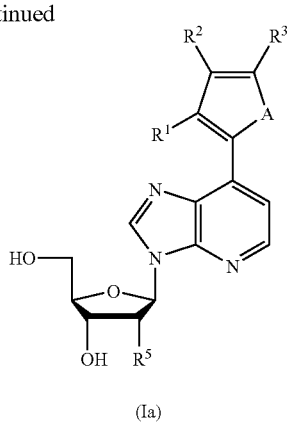

(Ia)

[wherein A represents an oxygen atom or a sulfur atom;
R$^1$, R$^2$ and R$^3$ each independently represent a hydrogen atom or a C$_1$-C$_4$ alkyl group;
R$^5$ represents a hydrogen atom or a hydroxyl group;
R$^6$ represents a hydrogen atom or a R$^9$O group; and
R$^7$, R$^8$ and R$^9$, which may be the same or different, each represent a protecting group for a hydroxyl group, such as an acetyl group, an isobutyryl group, a benzoyl group, a p-toluoyl group, a benzyl group, a trityl group, a dimethoxytrityl group or a t-butyldimethylsilyl group].

The compound of Formula (IIIa) (i.e., 2-amino-3-nitro-4-chloropyridine) is a known compound and can be synthesized using procedures known to those skilled in the art (see, e.g., Rec. Trav. Chim., 88, p. 1263-1274 (1963)).

In Scheme I, the first reaction for synthesizing a compound of Formula (IVa) from Formula (IIIa) is a coupling reaction between 2-amino-3-nitro-4-chloropyridine and a compound having a 2-thienyl or 2-furyl group. The second reaction for synthesizing a compound of Formula (Va) from Formula (IVa) is a reaction in which the nitro group at the 3-position of the pyridine ring is reduced to convert into an amino group. The third reaction for synthesizing a compound of Formula (VIIa) from Formula (Va) is a ring-closure reaction in which the compound of Formula (Va) is reacted with an orthoformic acid alkyl ester to form an imidazo[4,5-b]pyridine ring. The fourth reaction for synthesizing a compound of Formula (IIa) from Formula (VIIa) is a coupling reaction between the 3-position of the imidazo[4,5-b]pyridine ring and the 1-position of a ribose. These first to fourth reactions may be accomplished by using any synthesis technique well known to those skilled in the art.

In Scheme I, the fifth reaction for synthesizing a compound of Formula (Ia) from Formula (IIa) is a deprotection reaction of the hydroxyl groups in the ribose. Deprotection of the hydroxyl groups in the ribose may be accomplished by treatment with ammonia, methanolic ammonia, potassium hydroxide, sodium hydroxide, sodium methoxide, sodium ethoxide, hydrochloric acid, trifluoroacetic acid, tetrabutylammonium fluoride, boron tribromide, or hydrogen/palladium catalyst, etc. In a case where protecting groups for these hydroxyl groups are each an acetyl group, an isobutyryl group, a benzoyl group, a p-toluoyl group or the like, their deprotection may be accomplished by hydrolysis treatment with an acid or base, such as ammonia, methanolic ammonia, potassium hydroxide, sodium hydroxide, sodium methoxide or sodium ethoxide. Likewise, in a case where protecting groups for these hydroxyl groups are each a benzyl group, their deprotection may be accomplished by catalytic reduction with, e.g., hydrogen/palladium catalyst or by boron tribromide treatment. In a case where protecting groups are each a trityl group, a dimethoxytrityl group or the like, their deprotection may be accomplished by treatment with, e.g., trifluoroacetic acid or hydrochloric acid. Moreover, in a case where protecting groups for the ribose hydroxyl groups are each a t-butyldimethylsilyl group, their deprotection may be accomplished by treatment with tetrabutylammonium fluoride, sodium hydroxide, potassium hydroxide, etc. In this reaction, protecting groups for the ribose hydroxyl groups are each preferably an acetyl group, an isobutyryl group, a benzoyl group, a p-toluoyl group or the like and deprotected by treatment with methanolic ammonia. In this reaction, protecting groups for the ribose hydroxyl groups are more preferably p-toluoyl groups and deprotected by treatment with methanolic ammonia.

In another embodiment of the present invention, a 5-amino-3-(2-deoxy-β-D-ribofuranosyl)-3H-imidazo[4,5-b]pyridine derivative of Formula (Ib) according to the present invention, which has a heterocyclic ring as a substituent at the 7-position, may be synthesized through the synthetic pathway shown in the following reaction scheme (Scheme II):

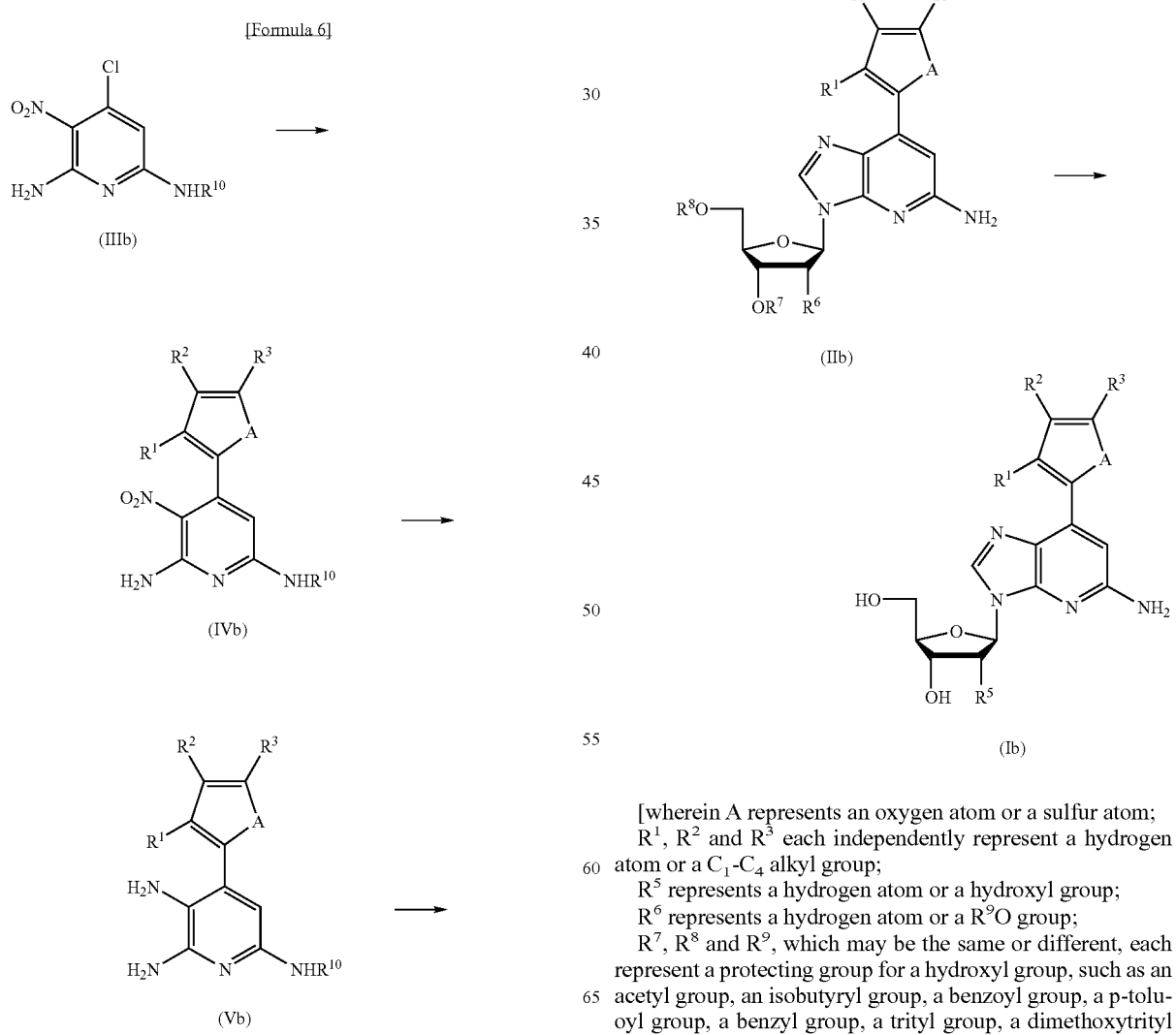

[wherein A represents an oxygen atom or a sulfur atom;
$R^1$, $R^2$ and $R^3$ each independently represent a hydrogen atom or a $C_1$-$C_4$ alkyl group;
$R^5$ represents a hydrogen atom or a hydroxyl group;
$R^6$ represents a hydrogen atom or a $R^9O$ group;
$R^7$, $R^8$ and $R^9$, which may be the same or different, each represent a protecting group for a hydroxyl group, such as an acetyl group, an isobutyryl group, a benzoyl group, a p-toluoyl group, a benzyl group, a trityl group, a dimethoxytrityl group or a t-butyldimethylsilyl group; and $R^{10}$ represents a protecting group for an amino group, such as an acetyl group, an isobutyryl group, a benzoyl group, a phenoxyacetyl group, an ethoxycarbonyl group, a t-butoxycarbonyl group or a benzyloxycarbonyl group].

In Scheme II, the first reaction for synthesizing a compound of Formula (IVb) from Formula (IIIb) is a coupling reaction between 2-amino-3-nitro-4-chloro-6-protected aminopyridine and a compound having a 2-thienyl or 2-furyl group. The second reaction for synthesizing a compound of Formula (Vb) from Formula (IVb) is a reaction in which the nitro group at the 3-position of the pyridine ring is reduced to convert into an amino group. The third reaction for synthesizing a compound of Formula (VIb) from Formula (Vb) is a ring-closure reaction in which the compound of Formula (Vb) is reacted with an orthoformic acid alkyl ester to form an imidazo[4,5-b]pyridine ring. The fourth reaction for synthesizing a compound of Formula (VIIb) from Formula (VIb) is a reaction in which the protected amino group at the 5-position of the imidazo[4,5-b]pyridine ring is deprotected to convert into an amino group. The fifth reaction for synthesizing a compound of Formula (IIb) from Formula (VIIb) is a coupling reaction between the 3-position of the imidazo[4,5-b] pyridine ring and the 1-position of a ribose. These first to fifth reactions may be accomplished by using any synthesis technique well known to those skilled in the art.

In Scheme II, the sixth reaction for synthesizing a compound of Formula (Ib) from Formula (IIb) is a deprotection reaction of the hydroxyl groups in the ribose. Deprotection of the hydroxyl groups in the ribose may be accomplished by treatment with ammonia, methanolic ammonia, potassium hydroxide, sodium hydroxide, sodium methoxide, sodium ethoxide, hydrochloric acid, trifluoroacetic acid, tetrabutylammonium fluoride, boron tribromide, or hydrogen/palladium catalyst, etc. With respect to a combination between a protecting group for a hydroxyl group and a reagent used for deprotection of the protecting group, the same combination as described for deprotection of the ribose hydroxyl groups in Scheme I may be selected. A combination preferred for deprotection of the ribose hydroxyl groups is as follows: protecting groups for the ribose hydroxyl groups are each an acetyl group, an isobutyryl group, a benzoyl group, a p-toluoyl group or the like and deprotected by treatment with methanolic ammonia. Protecting groups for the ribose hydroxyl groups in this reaction are more preferably p-toluoyl groups and deprotected by treatment with methanolic ammonia.

The present invention further provides an intermediate for preparing a compound of Formula (I) according to the present invention. The intermediate is a compound represented by Formula (II):

[Formula 7]

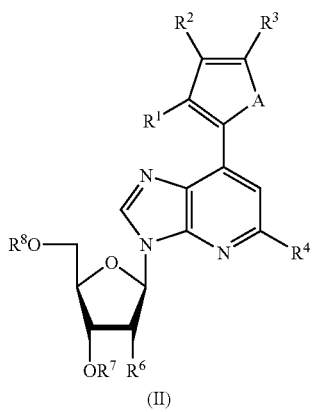

(II)

[wherein A represents an oxygen atom or a sulfur atom; $R^1$, $R^2$ and $R^3$ each independently represent a hydrogen atom or a $C_1$-$C_4$ alkyl group;

$R^4$ represents a hydrogen atom or an amino group;

$R^6$ represents a hydrogen atom or a $R^9O$ group;

$R^7$, $R^8$ and $R^9$, which may be the same or different, each represent a protecting group for a hydroxyl group, such as an acetyl group, an isobutyryl group, a benzoyl group, a p-toluoyl group, a benzyl group, a trityl group, a dimethoxytrityl group or a t-butyldimethylsilyl group]. In the above imidazo [4,5-b]pyridine derivative of the present invention represented by Formula (II), A is preferably a sulfur atom. Likewise, in the above imidazo[4,5-b]pyridine derivative of the present invention represented by Formula (II), any one of, desirably any two of, and more desirably all three of $R^1$, $R^2$ and $R^3$ are each preferably a hydrogen atom. The imidazo[4, 5-b]pyridine derivative of the present invention is more preferably a compound of Formula (II) shown above wherein A is a sulfur atom, and any one of, desirably any two of, and more desirably all three of $R^1$, $R^2$ and $R^3$ are each a hydrogen atom.

Among compounds of Formula (II), in particular, a compound wherein $R^4$ is a hydrogen atom is also represented herein by Formula (IIa) and a compound wherein $R^4$ is an amino group is also represented herein by Formula (IIb).

As defined herein, a pharmaceutically acceptable salt of the compound of the present invention may be any salt known in the art as a harmless salt, especially including an acid addition salt. A suitable acid addition salt may be formed, for example, by treating the compound of the present invention with an inorganic acid such as hydrochloric acid, hydrobromic acid, hydroiodic acid, sulfuric acid, nitric acid or phosphoric acid, or alternatively, with an organic acid such as acetic acid, maleic acid, succinic acid, mandelic acid, fumaric acid, malonic acid, pyruvic acid, oxalic acid, glycolic acid, salicylic acid, uronic acid (e.g., glucuronic acid or galacturonic acid), α-hydroxy acid (e.g., lactic acid, citric acid, gluconic acid or tartaric acid), amino acid (e.g., aspartic acid or glutamic acid), aromatic acid (e.g., benzoic acid or cinnamic acid), sulfonic acid (e.g., p-toluenesulfonic acid, methanesulfonic acid, ethanesulfonic acid or benzenesulfonic acid) or a similar acid. Salt preparation may be accomplished by using any appropriate technique known in the art.

The compound of Formula (I) according to the present invention has cancer cell growth inhibitory activity. Moreover, the cancer cell growth inhibitory activity of the compound of Formula (I) according to the present invention is dissociated from its growth inhibitory activity on normal cells, i.e., the compound has growth inhibitory activity that is lower in normal cells than in cancer cells. This means that the compound, when used at an appropriate concentration, can inhibit exclusively cancer cell growth without inhibiting normal cell growth.

The cell growth inhibitory activity of the compound of Formula (I) according to the present invention can be evaluated, for example, by the MTT assay well known to those skilled in the art (see, e.g., Seikagaku Jiten (Biochemical Dictionary), third edition, page 220, Tokyo Kagaku Dojin Co., Ltd., Japan, 2000). Briefly, the MTT assay is a technique for quantifying the number of living cells based on a phenomenon that light-yellow MTT (3-(4,5-dimethylthiazol-2-yl)-2, 5-diphenyltetrazolium bromide) is cleaved into dark-blue formazan by the action of mitochondrial reductase when taken up into living cells, whereas MTT cannot be cleaved in dead cells. The number of living cells is quantified by measuring the absorbance of formazan generated. In addition to MTT, WST-1 and Alamar Blue are used in the art as indicators for use in the MTT assay. When performed on the compound of the present invention, the MTT assay may be used with modifications.

Cancer cells which may be used to evaluate the cell growth inhibitory activity of the compound of Formula (I) according to the present invention include, but are not limited to, cultured cancer cells such as cultured human fibrosarcoma cells, cultured human acute lymphocytic leukemia CCRF-CEM cells, cultured human large intestine adenocarcinoma SW480 cells, cultured human alveolar cell carcinoma A549 cells, cultured human pancreatic adenocarcinoma PANC-1 cells, cultured human urinary bladder transitional cell carcinoma T24 cells, cultured human breast cancer MCF-7 cells, and cultured human liver cancer HuH7 cells. Preferred for use is cultured human fibrosarcoma cell line HT-1080. Normal cells which may be used to evaluate the cell growth inhibitory activity of the compound of the present invention include, but are not limited to, cells such as human fetal lung fibroblasts (normal diploid fibroblasts) and human peripheral blood lymphocytes. Preferred for use is human fetal lung fibroblast cell line WI-38.

The cell growth inhibitory activity of the compound of Formula (I) according to the present invention can be evaluated, for example, as follows. MTT assay is performed on each serially diluted test compound to measure the absorbance at 570 nm in the case of using MTT as an indicator, followed by calculating % inhibition for each concentration of the test compound according to the following equation.

$$\% \text{ Inhibition}=100\times[1-(\text{Abs}_{sample}-\text{Abs}_{background})/(\text{Abs}_{negative\ control}-\text{Abs}_{background})] \quad \text{[Expression 1]}$$

$\text{Abs}_{sample}$: Absorbance in the presence of test compound $\text{Abs}_{background}$: Absorbance in the absence of cells and test compound $\text{Abs}_{negative\ control}$: Absorbance in the absence of test compound The resulting % inhibition data for test compound concentrations is used to prepare a concentration-inhibition curve, from which the concentration required for each test compound to cause 50% inhibition of cell growth is then calculated as $IC_{50}$.

The cancer cell growth inhibitory activity of the compound of Formula (I) according to the present invention is dissociated from its growth inhibitory activity on normal cells. The compound of Formula (I) according to the present invention has a smaller $IC_{50}$ value for cancer cell growth inhibition than its $IC_{50}$ value for normal cells. Preferably, the compound of Formula (I) according to the present invention has an $IC_{50}$ value for cancer cell growth inhibition that is ⅔ or smaller, more preferably ½ or smaller, even more preferably ⅓ or smaller, still more preferably ¼ or smaller, yet more preferably ⅕ or smaller, and most preferably ¹⁄₁₀ or smaller than its $IC_{50}$ value for normal cells. This indicates that the compound is useful as an anticancer agent. Thus, the present invention provides a pharmaceutical composition comprising the compound of Formula (I) according to the present invention or a pharmaceutically acceptable salt thereof.

In a preferred embodiment, the pharmaceutical composition of the present invention is a pharmaceutical composition for cancer treatment, i.e., an anticancer agent. As used herein, the phrase "pharmaceutical composition for cancer treatment" means a pharmaceutical composition used for the purpose of curative treatment, alleviative treatment and prophylactic treatment of cancers. Curative treatment, alleviative treatment and prophylactic treatment of cancers include killing cancer cells, inhibiting cancer cell growth, blocking cancer metastasis, blocking cancer recurrence, or preventing cancerogenesis. As used herein, the term "cancer" means any malignant disease including a condition of excessive cell growth, and the terms "cancer", "tumor" and "neoplasia" are used interchangeably.

Examples of cancers treated by the pharmaceutical composition of the present invention include, but are not limited to: lung cancer; breast cancer; melanoma; sarcoma; fibrosarcoma; prostate cancer; cancer in the head and neck; cancer with unknown primary focus; lymphoma; leukemia; kidney cancer; cancer in the digestive tract such as esophageal cancer, gastric cancer, intestine cancer, colon cancer, anal cancer and rectal cancer; tumor in the brain; glioma; neuroblastoma; spongiocytoma; medulloblastoma; ependymoma; retinoblastoma; nasopharyngeal cancer; basal cell carcinoma; pancreatic cancer; bile duct cancer; Kaposi's sarcoma; thymoma; testis cancer; uterine cancer; vaginal cancer; uterine cervical cancer; ovarian cancer; liver cancer; endometrial cancer; vascular epithelioma; Hodgkin's lymphoma; non-Hodgkin's lymphoma; B-cell acute lymphoblastic leukemia/lymphoma; T-cell acute lymphoblastic leukemia/lymphoma; peripheral T-cell leukemia; adult T-cell leukemia/T-cell lymphoma; NK cell tumor; large granular lymphocytic leukemia; Langerhans' cell histiocytosis; bone marrow neoplasia; acute myelogenous leukemia; acute promyelocytic leukemia; acute myelomonocytic leukemia; acute monocytic leukemia; myelodysplastic syndrome; and chronic myeloproliferative disorder.

The pharmaceutical composition of the present invention may further comprise a pharmaceutically acceptable excipient, diluent or carrier. Such a pharmaceutically acceptable excipient, diluent or carrier is chemically inert and harmless either by nature or at the intended dosage, and hence does not affect the biological activity of the pharmaceutical composition of the present invention.

The pharmaceutical composition of the present invention may be incorporated with an excipient such as starch or lactose and formulated in the form of tablets, capsules, pills, powders, granules, troches, solutions, emulsions, suspensions or elixirs for oral administration including the sublingual route. The pharmaceutical composition of the present invention may be formulated in sustained-release, enteric-coated or immediate-release form. The pharmaceutical composition of the present invention may further comprise additional ingredients such as a coloring agent, a flavoring agent, a disintegrating agent, a granulation binder and a lubricant. These pharmaceutical compositions for oral administration may be readily prepared using techniques well known to those skilled in the art.

The pharmaceutical composition of the present invention may be formulated in the form of solutions or suspensions for parenteral administration, for example, by intravenous, intraarterial, intramuscular or subcutaneous injection or infusion. The pharmaceutical composition of the present invention formulated in the form of solutions or suspensions may also take the form of a lyophilized formulation which is dissolved and suspended in sterilized water or the like before use. Solutions or suspensions for injection or infusion are most preferably prepared in the form of an aseptic aqueous solution. Such solutions or suspensions for injection or infusion are prepared under dust-free and aseptic conditions, and adjusted to be isotonic with blood using other substances such as a buffer, a salt solution or glucose. Such solutions or suspensions for injection or infusion are also prepared to have a pH substantially equal to blood. Preparation of appropriate parenteral formulations under aseptic conditions may be readily accomplished by standard formulation techniques well known to those skilled in the art.

The pharmaceutical composition of the present invention may also be formulated in other forms such as solutions, suspensions, lotions, creams, ointments, gels, poultices, aerosols, sprays, suppositories or pessaries. Formulation into these forms is well known to those skilled in the art.

The present invention also relates to a method for cancer treatment using the compound or pharmaceutical composition of the present invention. As defined herein, cancer treatment includes curative treatment, alleviative treatment and prophylactic treatment. The compound or pharmaceutical composition of the present invention may be administered as a single dose or in divided doses. For oral and parenteral administration to human patients, the daily dose level of the compound of the present invention will be usually 1 to 100 mg/kg body weight, preferably 2.5 to 20 mg/kg body weight. However, the dose of the compound or pharmaceutical composition of the present invention will vary depending on various factors such as the age, body weight, health condition of individual patients, the severity of disease, and the patient's response to the compound of the present invention. The dose shown above is a dose in average cases, and administration at a higher or lower dose may also be appropriate in some cases. Administration at such a dose also falls within the scope of the present invention. A suitable dose of the compound or pharmaceutical composition of the present invention can be determined by doctors on the basis of the above or other factors.

Advantages of the Invention

The imidazo[4,5-b]pyridine derivatives of the present invention have high cancer cell growth inhibitory activity, whereas their cell growth inhibitory activity on normal cells is low. This indicates that the compounds of the present invention are useful as new anticancer agents.

EXAMPLES

The present invention will now be further described in the following examples, which are not intended to limit the technical scope of the invention. Based on the detailed description, various changes and modifications will be apparent to those skilled in the art, and such changes and modifications fall within the technical scope of the invention.

Example 1

Synthesis of 7-(2-thienyl)-3-(2-deoxy-1-β-D-ribofuranosyl)-3H-imidazo[4,5-b]pyridine (1-1) Synthesis of 2-amino-3-nitro-4-(2-thienyl)pyridine

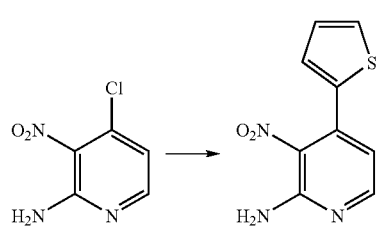

[Formula 8]

To a solution of 2-amino-3-nitro-4-chloropyridine (1.74 g, 10 mmol; which had been synthesized as described in Rec. Trav. Chim., 88, 1263-1274 (1963)) and dichlorobis(triphenylphosphine)palladium(II) (350 mg, 0.50 mmol) in DMF (50 ml), 2-(tributylstanyl)thiophene (3.82 ml, 12 mmol) was added under a nitrogen atmosphere and stirred at 100° C. for 4 hours. The solution was then poured into water (250 ml) and extracted three times with ethyl acetate (250 ml). The organic layers were dried over sodium sulfate and evaporated under reduced pressure to remove the solvent. The resulting residue was eluted by silica gel column chromatography with methylene chloride:ethyl acetate (100:0 to 49:1) to give 2-amino-3-nitro-4-(2-thienyl)pyridine (Rf 0.30/methylene chloride:ethyl acetate=19:1) (2.07 g, yield 93%).

$^1$H NMR (CDCl$_3$); δ 8.17 (d, J=5.1 Hz, 1H), 7.45 (dd, J=5.0 and 1.1 Hz, 1H), 7.12 (dd, J=3.6 and 1.1 Hz, 1H), 7.07 (dd, J=5.0 and 3.6 Hz, 1H), 6.77 (d, J=5.1 Hz, 1H), 5.66 (bs, 2H).

(1-2) Synthesis of 2,3-diamino-4-(2-thienyl)pyridine

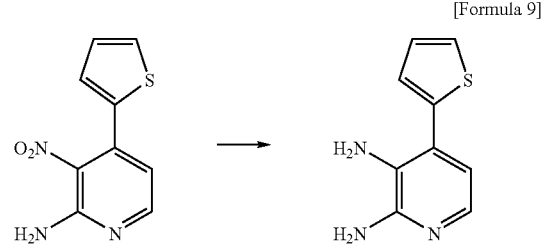

[Formula 9]

To a solution of 2-amino-3-nitro-4-(2-thienyl)pyridine (2.06 g, 9.3 mmol) and 10% palladium-carbon (466 mg) in ethanol (130 ml)-ethyl acetate (65 ml), a 1 M aqueous sodium borohydride solution was added at 0° C. The mixture was stirred at 0° C. for 1 hour and then poured into a 5% aqueous ammonium chloride solution (43 ml). The mixture was filtered through celite, and the filtrate was diluted with water (500 ml) and extracted three times with ethyl acetate (250 ml). The solution was dried over sodium sulfate and then evaporated under reduced pressure to remove the solvent. The residue was purified by column chromatography (methylene chloride:ethanol=19:1 to 93:7) to give 2,3-diamino-4-(2-thienyl)pyridine (Rf 0.24/methylene chloride:ethanol=9:1) (1.46 g, yield 82%).

$^1$H NMR (CDCl$_3$); δ 7.64 (d, J=5.1 Hz, 1H), 7.40 (dd, J=5.1 and 1.1 Hz, 1H), 7.23 (dd, J=3.5 and 1.1 Hz, 1H), 7.14 (dd, J=5.1 and 3.5 Hz, 1H), 6.74 (d, J=5.1 Hz, 1H), 4.26 (bs, 2H), 3.72 (bs, 2H).

(1-3) Synthesis of 7-(2-thienyl)-3H-imidazo[4,5-b]pyridine

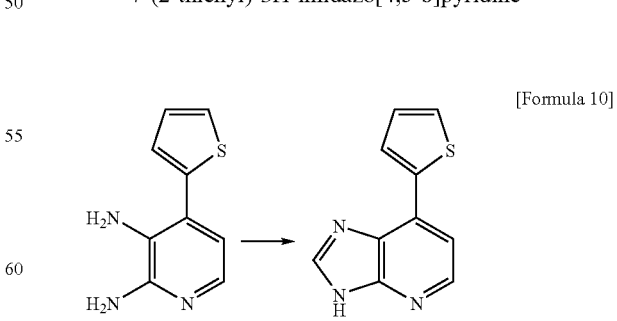

[Formula 10]

Hydrochloric acid (35 wt %, 1.47 ml) was added to 2,3-diamino-4-(2-thienyl)pyridine (1.46 g, 7.61 mmol) and orthoformic acid ethyl ester (40.5 ml). This solution was stirred at room temperature for 3 days and then filtered. The residue was washed with ether to give 7-(2-thienyl)-3H-imidazo[4,5-b]pyridine (1.74 g, 96%).

$^1$H NMR (DMSO-d$_6$); δ 8.77 (s, 1H), 8.42 (d, J=5.4 Hz, 1H), 8.25 (dd, J=3.6 and 1.2 Hz, 1H), 7.88 (dd, J=5.1 and 1.2 Hz, 1H), 7.66 (d, J=5.4 Hz, 1H), 7.31 (dd, J=5.1 and 3.6 Hz, 1H).

(1-4) Synthesis of 7-(2-thienyl)-3-[3,5-di-O-(p-toluoyl)-2-deoxy-1-β-D-ribofuranosyl]-3H-imidazo[4,5-b]pyridine

[Formula 11]

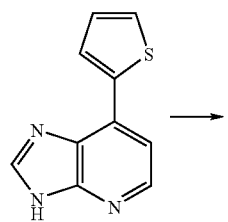

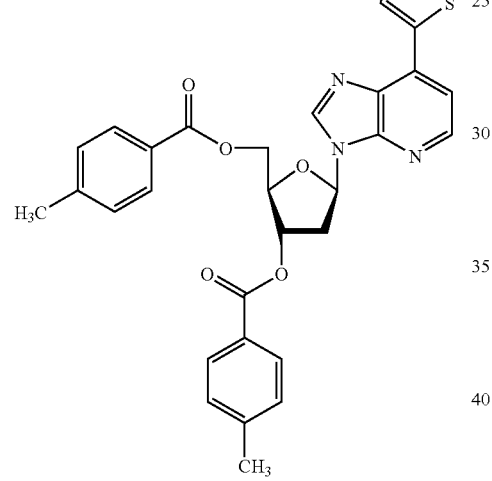

To a solution of 7-(2-thienyl)-3H-imidazo[4,5-b]pyridine (951 mg, 4.0 mmol) in acetonitrile (40 ml), sodium hydride (320 mg, 60% suspension in oil) was added, and the solution was stirred overnight at room temperature. To the solution, 2-deoxy-3,5-di-O-(p-toluoyl)-α-D-erythropentofuranosyl chloride (836 mg) was added and stirred for 90 minutes. The solution was poured into water (250 ml) and extracted three times with ethyl acetate (200 ml). The organic layers were dried over sodium sulfate and evaporated under reduced pressure to remove the solvent. The residue was purified by silica gel column chromatography (methylene chloride:ethanol=100:0 to 99:1) to give 7-(2-thienyl)-3-[3,5-di-O-(p-toluoyl)-2-deoxy-1-β-D-ribofuranosyl]-3H-imidazo[4,5-b]pyridine (Rf 0.38/methylene chloride:ethanol=49:1) (1.33 g, yield 60%).

$^1$H NMR (CDCl$_3$); δ 8.32 (d, J=5.3 Hz, 1H), 8.26 (s, 1H), 8.16 (dd, J=3.8 and 1.2 Hz, 1H), 7.93 (m, 4H), 7.50 (dd, J=5.1 and 1.2 Hz, 1H), 7.47 (d, J=5.3 Hz, 1H), 7.22 (m, 5H), 6.68 (dd, J=8.6 and 5.8 Hz, 1H), 5.82 (m, 1H), 4.69 (m, 3H), 3.18 (ddd, J=14.2, 8.6 and 6.4 Hz, 1H), 2.86 (ddd, J=14.2, 5.8 and 2.0 Hz, 1H), 2.43 (s, 3H), 2.37 (s, 3H).

(1-5) Synthesis of 7-(2-thienyl)-3-(2-deoxy-1-β-D-ribofuranosyl)-3H-imidazo[4,5-b]pyridine

[Formula 12]

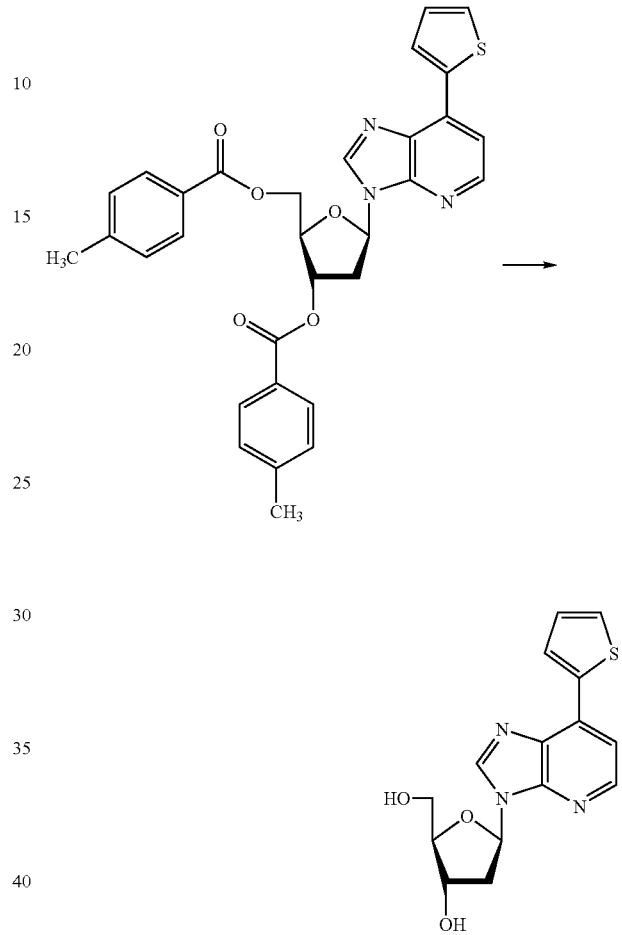

To 7-(2-thienyl)-3-[3,5-di-O-(p-toluoyl)-2-deoxy-1-β-D-ribofuranosyl]-3H-imidazo[4,5-b]pyridine (1.33 g, 2.40 mmol), methanolic ammonia (120 ml) was added at 0° C. and then stirred at room temperature for 2 days. After evaporation under reduced pressure to remove the solvent, the residue was purified by silica gel column chromatography (methylene chloride:ethanol=97:3 to 93:7) to give 7-(2-thienyl)-3-(2-deoxy-1-β-D-ribofuranosyl)-3H-imidazo[4,5-b]pyridine (717 mg, yield 94%).

$^1$H NMR (DMSO-d$_6$); δ 8.74 (s, 1H), 8.33 (d, J=5.1 Hz, 1H), 8.28 (dd, J=3.6 and 1.1 Hz, 1H), 7.82 (dd, J=5.1 and 1.1 Hz, 1H), 7.64 (d, J=5.1 Hz, 1H), 7.26 (dd, J=5.1 and 3.6 Hz, 1H), 6.25 (dd, J=7.3 and 6.4 Hz, 1H), 5.34 (bd, J=4.1 Hz, 1H), 5.11 (bt, J=5.4 Hz, 1H), 4.44 (m, 1H), 3.89 (m, 1H), 3.58 (m, 2H), 2.78 (ddd, J=13.0, 7.3 and 5.9 Hz, 1H), 2.24 (ddd, J=13.0, 6.4 and 3.0 Hz, 1H).

UV λ$_{max}$; 311 nm ε=2.04×10$^4$ in 25 mM sodium phosphate buffer (pH=6.8).

Example 2

Synthesis of 5-amino-7-(2-thienyl)-3-(2-deoxy-1-β-D-ribofuranosyl)-3H-imidazo[4,5-b]pyridine

(2-1) Synthesis of 2-amino-3-nitro-4-(2-thienyl)-6-ethoxycarbonylaminopyridine

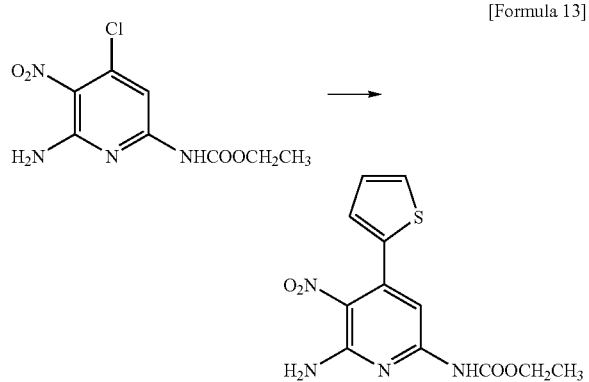

[Formula 13]

2-Amino-3-nitro-4-chloro-6-ethoxycarbonylaminopyridine (1.30 g, 5.0 mmol) and dichlorobis(triphenylphosphine)palladium(II) (175 mg, 0.25 mmol) were dissolved in DMF (30 ml). To this solution, 2-(tributylstanyl)thiophene (1.91 ml, 6.0 mmol) was added under an argon atmosphere and stirred at 100° C. for 2 hours. This mixture was poured into water (100 ml) and extracted three times with ethyl acetate (8100 ml). The organic layers were dried over sodium sulfate, followed by silica gel column chromatography (methylene chloride:ethyl acetate=100:0 to 99:1) to purify the desired product, 2-amino-3-nitro-4-(2-thienyl)-6-ethoxycarbonylaminopyridine (Rf 0.52/methylene chloride:ethyl acetate=19:1) (1.96 g, yield 85%).

$^1$H NMR (DMSO-$d_6$); δ 10.33 (bs, 1H), 7.70 (m, 1H), 7.24 (s, 1H), 7.10 (m, 2H), 7.02 (bs, 2H), 4.13 (q, J=7.0 Hz, 2H), 1.22 (t, J=7.0 Hz, 3H).

(2-2) Synthesis of 2,3-diamino-4-(2-thienyl)-6-ethoxycarbonylaminopyridine

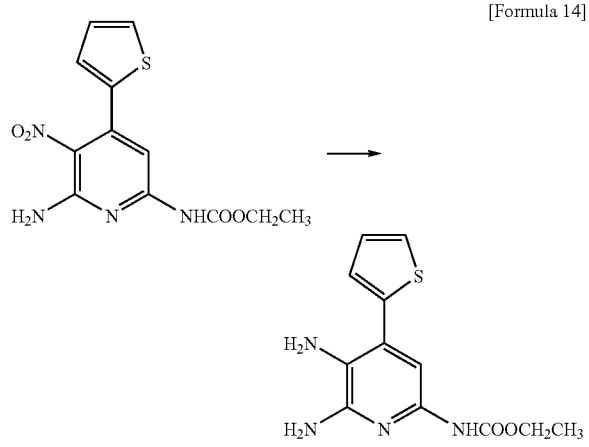

[Formula 14]

2-Amino-3-nitro-4-(2-thienyl)-6-ethoxycarbonylaminopyridine (1.57 g, 5.1 mmol) and 10% palladium-carbon (255 mg) were dissolved in ethanol (77 ml)-ethyl acetate (38 ml). To this mixture, a 1 M aqueous sodium borohydride solution (15.3 ml) was added at 0° C. and stirred at 0° C. for 1 hour. This solution was mixed with a 5% aqueous ammonium chloride solution (23.4 ml) and filtered through celite. The celite was washed with water (204 ml). The filtrate and this washing solution were mixed and evaporated under reduced pressure to remove ethanol and ethyl acetate, followed by extraction three times with ethyl acetate (150 ml). This solution was dried over sodium sulfate and evaporated under reduced pressure to remove the solvent, followed by silica gel column chromatography (methylene chloride:ethyl acetate=7:3 to 1:1) to purify the desired product, 2,3-diamino-4-(2-thienyl)-6-ethoxycarbonylaminopyridine (Rf 0.39/methylene chloride:ethyl acetate=1:2) (1.28 g, yield 90%).

$^1$H NMR (DMSO-$d_6$); δ 9.07 (bs, 1H), 7.60 (dd, J=5.1 and 1.1 Hz, 1H), 7.34 (dd, J=3.7 and 1.1 Hz, 1H), 7.16 (dd, J=5.1 and 3.7 Hz, 1H), 6.96 (s, 1H), 5.59 (bs, 2H), 4.38 (bs, 2H), 4.04 (q, J=7.0 Hz, 2H), 1.18 (t, J=7.0 Hz, 3H).

(2-3) Synthesis of 7-(2-thienyl)-5-ethoxycarbonylamino-3H-imidazo[4,5-b]pyridine

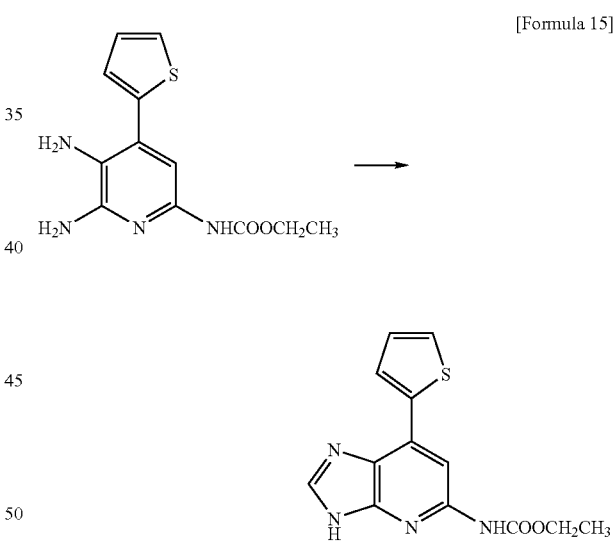

[Formula 15]

Hydrochloric acid (35 wt %, 892 μl) was added to 2,3-diamino-4-(2-thienyl)-6-ethoxycarbonylaminopyridine (1.28 g, 4.61 mmol) and orthoformic acid ethyl ester (24.6 ml), followed by stirring at room temperature for 3 days. This solution was filtered and the product was washed with ether to give 7-(2-thienyl)-5-ethoxycarbonylamino-3H-imidazo[4,5-b]pyridine (1.36 g, yield 91%).

$^1$H NMR (DMSO-$d_6$); δ 10.25 (bs, 1H), 8.69 (bs, 1H), 8.20 (dd, J=3.8 and 1.1 Hz, 1H), 8.12 (s, 1H), 7.81 (dd, J=5.1 and 1.1 Hz, 1H), 7.28 (dd, J=5.1 and 3.8 Hz, 1H), 4.17 (q, J=7.2 Hz, 2H), 1.26 (t, J=7.2 Hz, 3H).

(2-4) Synthesis of 5-amino-7-(2-thienyl)-3H-imidazo[4,5-b]pyridine

[Formula 16]

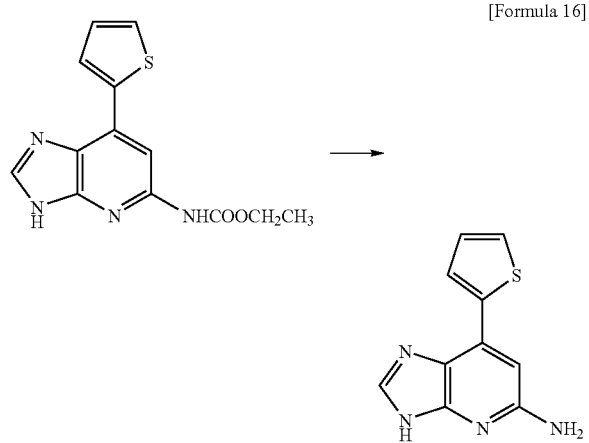

To a solution of 7-(2-thienyl)-5-ethoxycarbonylamino-3H-imidazo[4,5-b]pyridine (1.21 g, 3.72 mmol) in ethanol (130 ml), potassium hydroxide (7.29 g) was added and heated under reflux for 4 hours. To this solution, an aqueous ammonium chloride solution (7.65 g/26 ml) was added, followed by evaporation under reduced pressure to remove the solvent. The product was isolated by silica gel column chromatography (methylene chloride:ethanol=9:1 to 7:3) to give 5-amino-7-(2-thienyl)-3H-imidazo[4,5-b]pyridine (870 mg).

$^1$H NMR (DMSO-d$_6$); δ 12.35 (bs, 1H), 8.19 (dd, J=3.6 and 0.9 Hz, 1H), 7.95 (s, 1H), 7.67 (dd, J=5.1 and 0.9 Hz, 1H), 7.20 (dd, J=5.1 and 3.6 Hz, 1H), 6.64 (s, 1H), 5.86 (bs, 2H).

(2-5) Synthesis of 5-amino-7-(2-thienyl)-3-[3,5-di-O-(p-toluoyl)-2-deoxy-1-β-D-ribofuranosyl]-3H-imidazo[4,5-b]pyridine

[Formula 17]

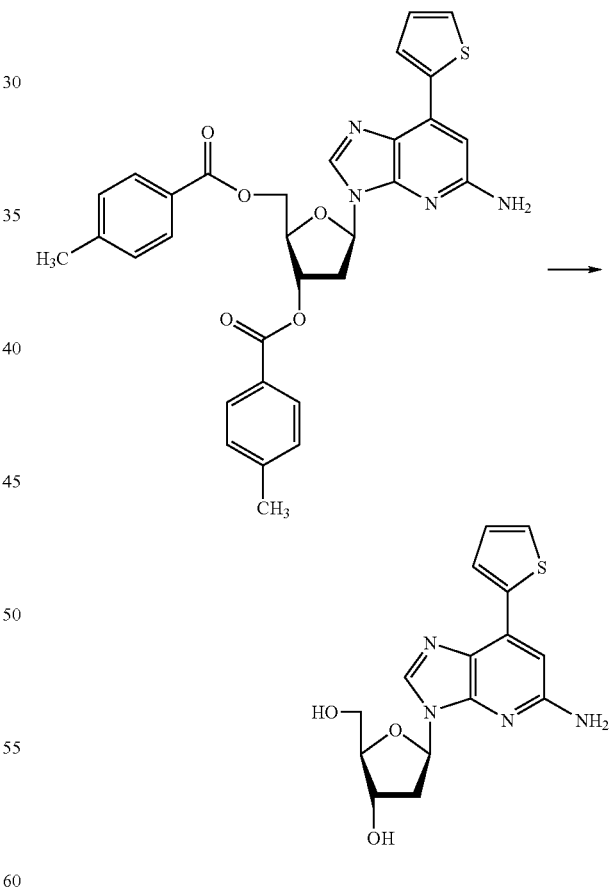

To a solution of 5-amino-7-(2-thienyl)-3H-imidazo[4,5-b]pyridine (465 mg, 2.15 mmol) in acetonitrile (22 ml), sodium hydride (86 mg, 60% suspension in oil) was added and stirred at room temperature for 6 hours. To this mixture, 2-deoxy-3,5-di-O-(p-toluoyl)-α-D-erythropentofuranosyl chloride (836 mg) was added and stirred at room temperature for 1 hour. This solution was poured into water (100 ml) and extracted three times with methylene chloride (100 ml). This solution was dried over sodium sulfate and then evaporated to remove the solvent. The product was isolated by silica gel column chromatography (methylene chloride:ethyl acetate=19:1 to 37:3) to give 5-amino-7-(2-thienyl)-3-[3,5-di-O-(p-toluoyl)-2-deoxy-1-β-D-ribofuranosyl]-3H-imidazo[4,5-b]pyridine (Rf 0.37/methylene chloride:ethyl acetate=9:1) (1.05 g, yield 86%).

$^1$H NMR (CDCl$_3$); δ 8.10 (dd, J=3.6 and 1.1 Hz, 1H), 7.94 (m, 5H), 7.44 (dd, J=5.1 and 1.1 Hz, 1H), 7.23 (m, 4H), 7.16 (dd, J=5.1 and 3.6 Hz, 1H), 6.50 (dd, J=8.4 and 5.7 Hz, 1H), 5.82 (m, 1H), 4.85 (dd, J=13.2 and 6.2 Hz, 1H), 4.64 (m, 2H), 4.53 (bs, 2H), 3.26 (ddd, J=14.1, 8.4 and 5.9 Hz, 1H), 2.68 (ddd, J=14.1, 5.7 and 1.9 Hz, 1H), 2.40 (s, 3H), 2.37 (s, 3H).

(2-6) Synthesis of 5-amino-7-(2-thienyl)-3-(2-deoxy-1-β-D-ribofuranosyl)-3H-imidazo[4,5-b]pyridine

[Formula 18]

To 5-amino-7-(2-thienyl)-3-[3,5-di-O-(p-toluoyl)-2-deoxy-1-β-D-ribofuranosyl]-3H-imidazo[4,5-b]pyridine (1.05 g, 1.85 mmol), methanolic ammonia (92 ml) was added and stirred at room temperature for 2 hours. After evaporation under reduced pressure to remove the solvent, the product was purified by silica gel column chromatography (methylene chloride:ethanol=19:1 to 9:1) to give 5-amino-7-(2-thienyl)-3-(2-deoxy-1-β-D-ribofuranosyl)-3H-imidazo[4,5-b]pyridine (555 mg, yield 90%).

$^1$H NMR (DMSO-$d_6$); δ 8.24 (s, 1H), 8.19 (dd, J=3.5 and 1.1 Hz, 1H), 7.70 (dd, J=5.0 and 1.1 Hz, 1H), 7.21 (dd, J=5.0 and 3.5 Hz, 1H), 6.70 (s, 1H), 6.33 (dd, J=8.1 and 6.1 Hz, 1H), 6.03 (bs, 2H), 5.28 (bd, J=3.2 Hz, 1H), 5.07 (bt, J=5.4 Hz, 1H), 4.38 (m, 1H), 3.84 (m, 1H), 3.55 (m, 2H), 2.64 (ddd, J=13.1, 6.1 and 5.7 Hz, 1H), 2.24 (ddd, J=13.1, 5.9 and 3.0 Hz, 1H).

UV $\lambda_{max}$; 307 nm ε=2.11×10$^4$, 247 nm ε=1.44×10$^3$, 222 nm ε=1.70×10$^4$ in 25 mM sodium phosphate buffer (pH=6.8).

Example 3

Test for Cell Growth Inhibitory Activity

MTT assay was performed to examine two test compounds, i.e., 7-(2-thienyl)-3-(2-deoxy-1-β-D-ribofuranosyl)-3H-imidazo[4,5-b]pyridine (herein referred to as Compound IA) and 5-amino-7-(2-thienyl)-3-(2-deoxy-1-β-D-ribofuranosyl)-3H-imidazo[4,5-b]pyridine (herein referred to as Compound IB) for their cell growth inhibitory effect on cultured human fibrosarcoma HT-1080 cells and human fetal lung fibroblast (normal diploid fibroblast) WI-38 cells. These cells (1×10$^4$ cells/ml) were seeded in 96-well microplates (IWAKI) at 90 µl/well. After culturing at 37° C. for 3 to 4 hours, test compound solutions (10 µl each), which had been dissolved in PBS-5% DMSO and adjusted to various concentrations, were added and incubated at 37° C. for 72 hours. To the wells containing these solutions, a PBS solution of MTT (5 mg/ml) was added in 25 µl volumes and incubated at 37° C. for an additional 2 hours, followed by addition of a 50% DMF-20% SDS solution in 100 µl to each well. After incubation was continued at 37° C. for 16 hours, the absorbance at 570 nm was measured using a microplate reader to calculate % inhibition according to the following equation.

% Inhibition=100×[1−($Abs_{sample}$−$Abs_{background}$)/($Abs_{negative\ control}$−$Abs_{background}$)]     [Expression 2]

$Abs_{sample}$: Absorbance in the presence of test compound $Abs_{background}$: Absorbance in the absence of cells and test compound $Abs_{negative\ control}$: Absorbance in the absence of test compound The concentration (IC$_{50}$ µM) required for each test compound to cause 50% inhibition of cell growth was calculated from a concentration-inhibition curve. The IC$_{50}$ values are shown in Table 1 below, along with their standard deviation.

TABLE 1

| Compound | IC$_{50}$ µM | |
|---|---|---|
|  | HT-1080 cell | WI-38 cell |
| Compound IA | 62 ± 6 | 290 ± 130 |
| Compound IB | 34 ± 6 | 330 ± 40 |

As shown in Table 1, Compounds IA and IB had IC$_{50}$ values of 62 µM and 34 µM, respectively, for cultured human fibrosarcoma HT-1080 cells. On the other hand, each compound had an IC$_{50}$ value of around 300 µM for the normal cells, human fetal lung fibroblast (normal diploid fibroblast) WI-38 cells. This indicates that Compound IB has about 10-fold higher growth inhibitory activity on cancer cells than on normal cells, while Compound IA has about 5-fold higher growth inhibitory activity on cancer cells than on normal cells. Thus, the cancer cell growth inhibitory activity of these compounds is dissociated from their cell growth inhibitory activity on normal cells.

The invention claimed is:

1. A method for synthesizing a compound of the Formula Ia,

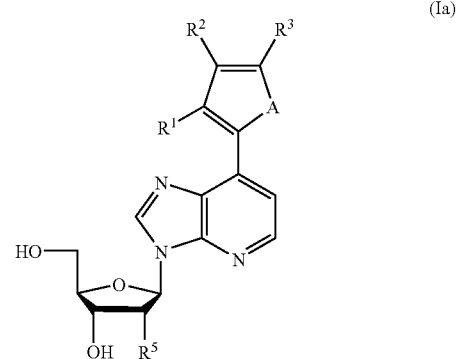

or a pharmaceutically acceptable salt thereof comprising performing reactions of a synthetic path

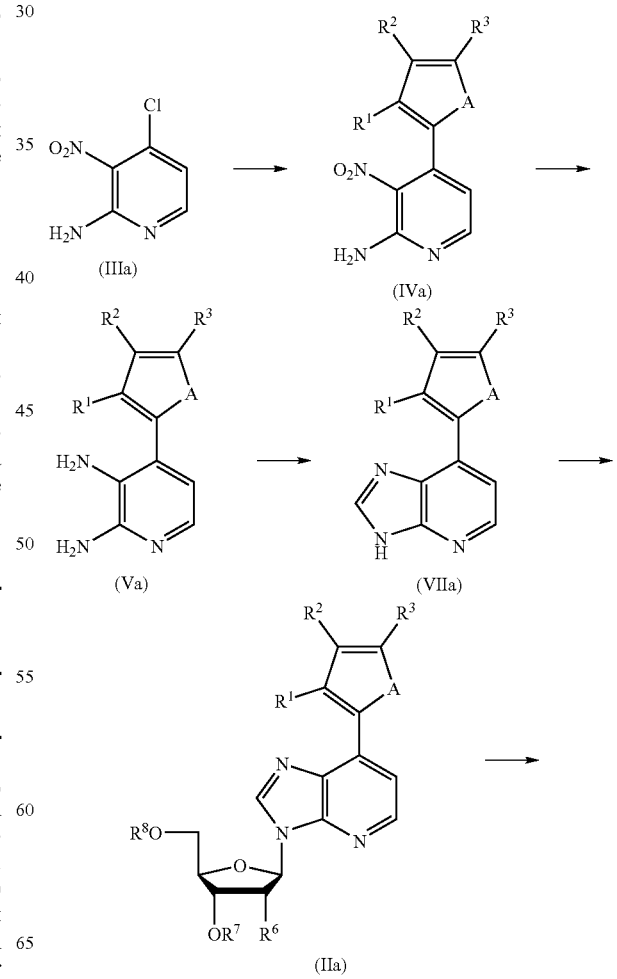

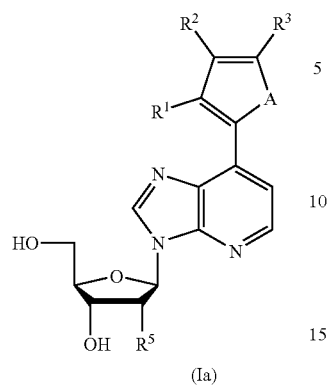

(Ia)

wherein A represents an oxygen atom or a sulfur atom;
$R^1$, $R^2$ and $R^3$ each independently represent a hydrogen atom or a $C_1$-$C_4$ alkyl group;
$R^5$ represents a hydrogen atom or a hydroxyl group;
$R^6$ represents a hydrogen atom or a $OR^9$ group; and
$R^7$, $R^8$ and $R^9$, which may be the same or different, each represent a protecting group for a hydroxyl group.

2. The method of claim 1, in which $R^7$, $R^8$ and $R^9$ are selected from the group consisting of an acetyl group, an isobutyryl group, a benzoyl group, a p-toluoyl group, a benzyl group, a trityl group, a dimethoxytrityl group and a t-butyldimethylsilyl group.

3. A method for synthesizing the compound represented by Formula (Ib):

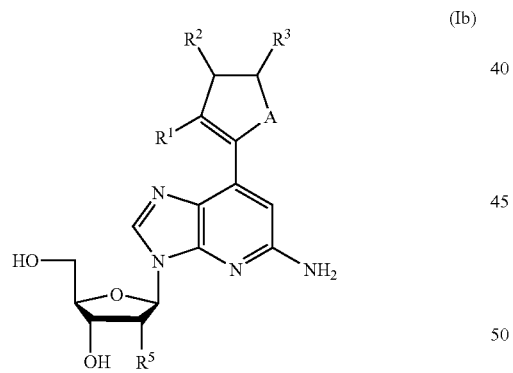

(Ib)

or a pharmaceutically acceptable salt thereof, comprising performing reactions of a synthetic path

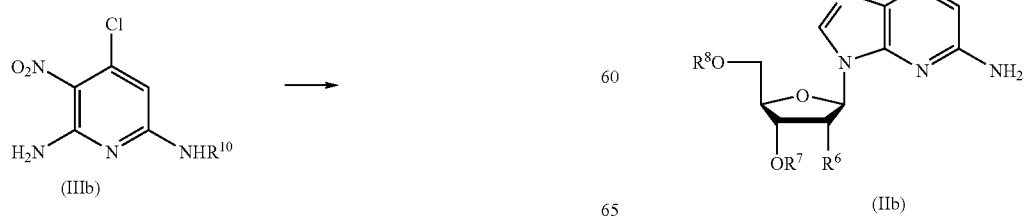

(IIIb)

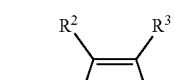
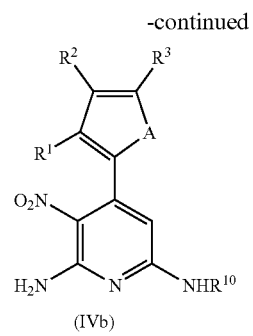

(IVb)

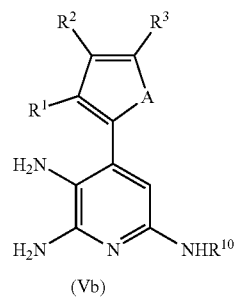

(Vb)

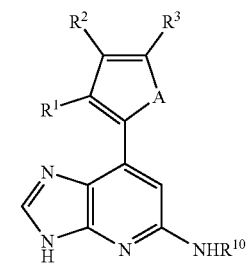

(VIb)

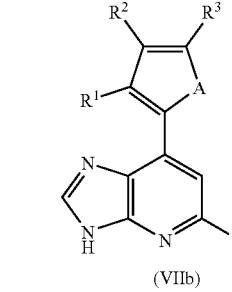

(VIIb)

-continued

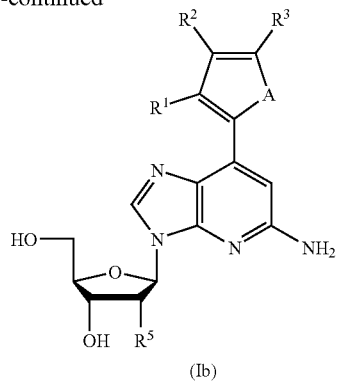

(Ib)

wherein A represents an oxygen atom or a sulfur atom;
R$^1$, R$^2$ and R$^3$ each independently represent a hydrogen atom or a C$_1$-C$_4$ alkyl group;
R$^5$ represents a hydrogen atom or a hydroxyl group;
R$^6$ represents a hydrogen atom or a OR$^9$ group;
R$^7$, R$^8$ and R$^9$, which may be the same or different, each represent a protecting group for a hydroxyl group; and
R$^{10}$ represents a protecting group for an amino group.

4. The method of claim 3, in which R$^7$, R$^8$ and R$^9$ are selected from the group consisting of an acetyl group, an isobutyryl group, a benzoyl group, a p-toluoyl group, a benzyl group, a trityl group, a dimethoxytrityl group and a t-butyldimethylsilyl group.

5. The method of claim 3, in which R$^{10}$ is selected from the group consisting of an acetyl group, an isobutyryl group, a benzoyl group, a phenoxyacetyl group, an ethoxycarbonyl group, a t-butoxycarbonyl group and a benzyloxycarbonyl group.

6. The method of claim 4, in which R$^{10}$ is selected from the group consisting of an acetyl group, an isobutyryl group, a benzoyl group, a phenoxyacetyl group, an ethoxycarbonyl group, a t-butoxycarbonyl group and a benzyloxycarbonyl group.

7. A compound represented by Formula (I):

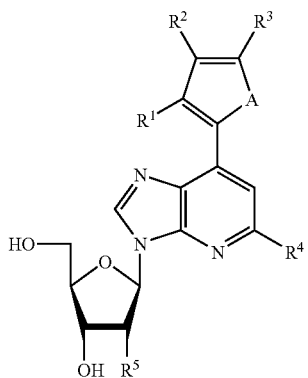

(I)

wherein A represents an oxygen atom or a sulfur atom;

R$^1$, R$^2$ and R$^3$ each independently represent a hydrogen atom or a C$_1$-C$_4$ alkyl group;
R$^4$ represents a hydrogen atom or an amino group; and
R$^5$ represents a hydrogen atom or a hydroxyl group,
or a pharmaceutically acceptable salt thereof.

8. The compound according to claim 7 or a pharmaceutically acceptable salt thereof, wherein the compound is: 7-(2-thienyl)-3-(2-deoxy-β-D-ribofuranosyl)-3H-imidazo[4,5-b]pyridine or 5-amino-7-(2-thienyl)-3-(2-deoxy-β-D-ribofuranosyl)-3H-imidazo[4,5-b]pyridine.

9. A compound represented by Formula (II):

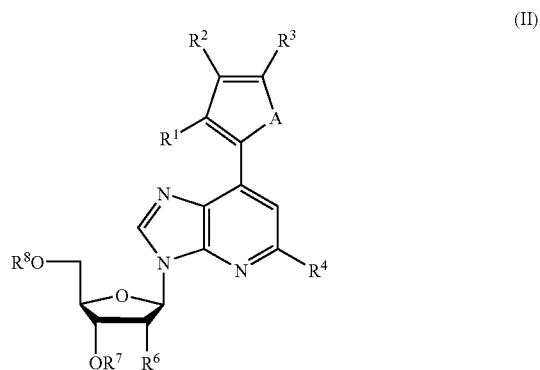

(II)

wherein A represents an oxygen atom or a sulfur atom;

R$^1$, R$^2$ and R$^3$ each independently represent a hydrogen atom or a C$_1$-C$_4$ alkyl group;

R$^4$ represents a hydrogen atom or an amino group;

R$^6$ represents a hydrogen atom or an OR$^9$ group: and

R$^7$, R$^8$ and R$^9$, which may be the same or different, each are selected from the group consisting of an acetyl group, an isobutyryl group, a benzoyl group, a p-toluoyl group, a benzyl group, a trityl group, a dimethoxytrityl group and a t-butyldimethylsilyl group.

* * * * *

UNITED STATES PATENT AND TRADEMARK OFFICE
CERTIFICATE OF CORRECTION

| | | Page 1 of 1 |
|---|---|---|
| PATENT NO. | : 7,615,628 B2 | |
| APPLICATION NO. | : 11/795554 | |
| DATED | : November 10, 2009 | |
| INVENTOR(S) | : Ichiro Hirao et al. | |

It is certified that error appears in the above-identified patent and that said Letters Patent is hereby corrected as shown below:

In the Specifications

Column 1, line 9 reading:

"Japanese patent application 2005/01265 filed Jan. 20, 2005" should read --Japanese patent application 2005/012685 filed Jan. 20, 2005--

Signed and Sealed this
Fifteenth Day of April, 2014

Michelle K. Lee
*Deputy Director of the United States Patent and Trademark Office*